United States Patent [19]

Abts

[11] 4,237,720
[45] * Dec. 9, 1980

[54] ULTRASONIC PARTICULATE SENSING

[75] Inventor: Leigh R. Abts, Providence, R.I.

[73] Assignee: Rhode Island Hospital, Providence, R.I.

[*] Notice: The portion of the term of this patent subsequent to Sep. 12, 1995, has been disclaimed.

[21] Appl. No.: 931,478

[22] Filed: Aug. 7, 1978

Related U.S. Application Data

[63] Continuation of Ser. No. 792,669, May 2, 1977, Pat. No. 4,112,773.

[51] Int. Cl.³ ............................................. G01N 29/02
[52] U.S. Cl. ......................................................... 73/19
[58] Field of Search ..................... 73/19, 61 R, 194 A; 128/214 E, 2.05 Z, 2 V, 660

[56] References Cited

U.S. PATENT DOCUMENTS

| | | | |
|---|---|---|---|
| 3,204,458 | 9/1965 | Gillen | 73/194 A |
| 3,269,172 | 8/1966 | McGaughey | 73/61 R |
| 3,774,717 | 11/1973 | Chodorow | 73/597 |
| 3,821,834 | 7/1974 | McElroy | 73/632 |
| 3,898,637 | 8/1965 | Wolstenholme | 128/214 E |
| 3,974,681 | 8/1976 | Namery | 73/19 |
| 4,068,521 | 1/1978 | Cosentino et al. | 73/19 |

FOREIGN PATENT DOCUMENTS 2240342  3/1974  Fed. Rep. of Germany .............. 73/19

OTHER PUBLICATIONS

J. T. McElroy, "Focused Ultrasonic Beams", Automation Industries, Inc. Brochure, pp. 6-16, Sep. 1966.

Patterson et al., "Microemboli During Cardiopulmonary Bypass Detected By Ultrasound", Surg., Gyn. and Obs., 129: 505-510, 1969.

Szabo et al., "Arterial Blood Filter Evaluation By Echo-Ultrasound", Proc. 27th Annual Conference On Engineering In Medicine and Biology", 16: 191, 1974.

Primary Examiner—Stephen A. Kreitman

[57] ABSTRACT

A pulse echo device with a concave transmitter-receiver surface located to direct ultrasonic energy to a focal point spaced therefrom transversely of a conduit, the focal point being a distance transversely of the conduit less than twice the thickness of the conduit.

6 Claims, 3 Drawing Figures

U.S. Patent    Dec. 9, 1980    4,237,720 ured piezoelectric transmitter is coupled with a con-
ULTRASONIC PARTICULATE SENSING This is a continuation of application Ser. No. 792,669, filed May 2, 1977, now U.S. Pat. No. 4,112,773.

This invention relates to obtaining information about matter discontinuities in flowing fluid streams.

FIELD OF THE INVENTION

In particular, this invention relates to determining such things as the number and size of such discontinuities, for example microembolisms in blood flowing in a conduit.

BACKGROUND OF THE INVENTION

Pulse-echo ultrasonic search units are well known, particularly in nondestructive testing systems; bursts or pulses emitted by such units are detected when reflected back from discontinuities, such as inclusions, as disclosed in Automation Industries' McElroy U.S. Pat. No. 3,821,834, "Method of Making an Ultrasonic Search Unit", granted July 2, 1974. Pulse-echo ultrasonic search units have also been used to measure particles in liquid, as taught in the same company's McGaughey et al. U.S. Pat. No. 3,269,172, "Apparatus for Measuring Particles in Liquids", granted Aug. 30, 1966. A generally similar approach was used to measure discontinuities in blood flowing in a conduit by Patterson et al. ("Microemboli during cardiopulmonary bypass detected by ultrasound", Surg., Gyn. & Obs., 129: 505–510, 1969) and by Szabo et al. ("Arterial blood filter evaluation by echo-ultrasound", Proc. 27th Annual Conference on Engineering in Medicine and Biology, 160: 191, 1974). McGaughey, Patterson et al., and Szabo et al. each of them directed the transmitted signal coaxially longitudinally of the conduit, with a focal point many times the diameter of the conduit in distance from the search unit's transmitting surface. Furthermore, they used flat or convex transmitting surfaces.

SUMMARY OF THE INVENTION

I have discovered that discontinuities in fluid flowing in a conduit can be detected with greatly improved sensitivity, yet with great simplicity, by providing in a pulse echo device a concave transmitting surface arranged to transmit generally across a conduit, with a focal length of not over twice the distance across the conduit. In preferred embodiments a search unit working with a pulse transmitting surface continuous with a surface of the conduit directs transmission across the conduit. In the most preferred embodiment, a flat-surfaced piezoelectric transmitter is coupled with a concave cylindrical lens, integral with the rest of the wall of a cylindrical conduit, to provide the transmitting surface, and the focal length is less than the diameter of the conduit.

The invention is especially useful in evaluating very small particles or other discontinuities (e.g., bubbles in liquid) present in very small quantity. It has advantages of sensitivity, high field density, simplicity, and relative freedom from eddies and other turbulence.

DESCRIPTION OF PREFERRED EMBODIMENTS

The structure and operation of preferred embodiments of the invention are as follows.

STRUCTURE

The drawings show the preferred embodiments, then described.

1. Drawings

2. Description

Figure 1:
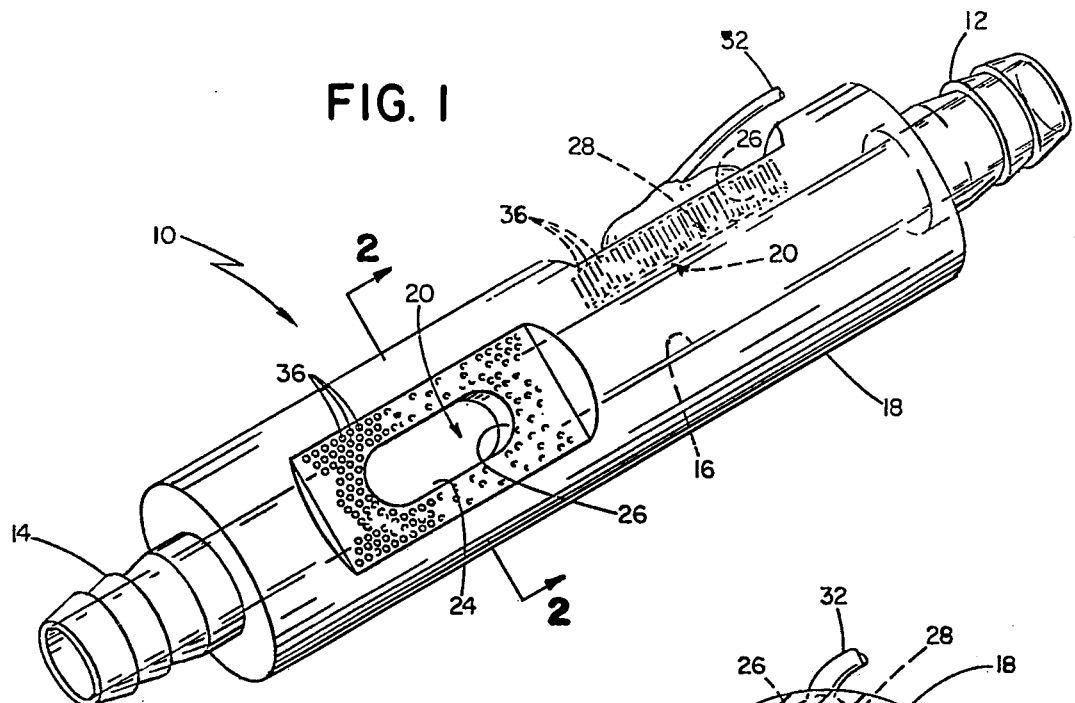
FIG. 1 is an isometric view of the most preferred embodiment of the invention, with one of its crystals, and associated wire and potting, omitted.
Figure 2:
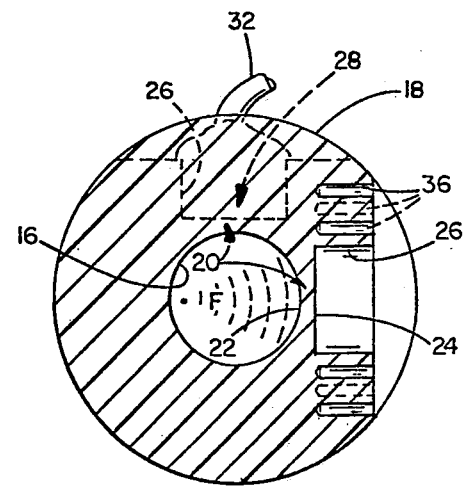
FIG. 2 is an enlarged sectional view therethrough, at 2—2.

Turning now to FIGS. 1 and 2, there is shown a transparent methyl methacrylate blood-conducting unit 10 with end portions 12, 14 to cooperate with tubing. A polished cylindrical blood passage 16, $\frac{1}{2}$" in diameter and $4\frac{1}{2}$" in length, is defined by wall 18 and the end portions. Integral with wall 18 are two lenses 20 with cylindrically concave inner surfaces 22 (chosen to focus the field of sound F on a line inside passage 16 near the opposite wall 18 thereof) and planar upper surfaces 24. The latter are provided by a pair of blind grooves 26 cut into wall 18 to extend along centerlines longitudinally and radially thereof, said centerlines being along radii of the unit 10 displaced 90° from each other. The minimum lens thickness, defined by the separation between surfaces 22 and 24 along said centerlines, is 0.010 inch.

Seated in grooves 26 are ceramic piezoelectric crystals 28 and 30, acoustically coupled to lenses 20 and electrically connected as is conventional with, e.g., wire 32.

Surrounding each groove 26 are three closely spaced rows of blind holes 36. These holes are 1 mm. in diameter, extend generally parallel to the walls of grooves 26, and do not extend into passage 16.

The crystals may suitably be formed from round ceramic crystals sold by Keramos, Incorporated, 104 N. Church St., Lizton, Indiana, under the trade designation K 81. These are preferably electrically connected in a pulser-receiver unit mounted in a reflectoscope sold by the aforementioned Automation Industries, of Shelter Rock Road, Danbury, Connecticut (Model UM 771-B).

Figure 3:
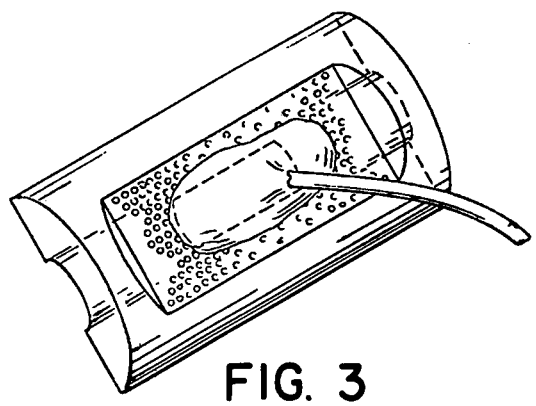
FIG. 3 is a three-dimensional view of another embodiment of the invention.

In FIG. 3 is shown a half annulus of methyl methacrylate; it is provided with one blind groove, a crystal, a lens, and a multiplicity of blind holes, all just as in the embodiment of FIGS. 1 and 2.

OPERATION

In operation, each crystal may as desired be energized to give a 5 megahertz output for two microseconds, to transmit through its associated lens an ultrasonic pulse of that duration. Any reflection received may be displayed on an oscilloscope portion of the reflectoscope. The shapes of the curves generated provide information about discontinuities in blood flowing through the passage. Thus number of peaks reflects number of particles and increased amplitude reflects increased particle size, particularly in situations in which only one particle is ordinarily within the field of focus (shaded, at F) at any given time. The reflectoscope oscilloscope permits visual observation giving useful information. Provision of the two pulse echo stations 90° apart facilitates determining further the shape of a particular particle. Holes 36 damp acoustic impulses passing in directions toward them.

The embodiment of FIG. 3 is used in much the same way, except that in it the transmitting surface is not a part of the fluid conduit wall. This unit may be placed alongside (e.g.) a blood vessel to detect discontinuities flowing therein.

OTHER EMBODIMENTS

The passage wall and lens may be made of material transparent to ultrasound but not to light. The crystal itself may be formed with a concave transmitting surface. Signal output may be taken to a computer programmed to print out information.

What is claimed is:

1. A pulse echo device for detecting the presence of small particles in a flowing stream of fluid, comprising
   a conduit for receiving said stream of fluid,
   acoustical transducer means for transmitting ultrasonic energy transversely into said stream along a first direction and for receiving ultrasonic energy reflected by said particles and returning from said stream along a second direction generally opposite said first direction, said transducer means including at least one acoustical transducer mounted on said conduit, and
   acoustic damping means spaced from and surrounding said transducer in directions other than said first transmission direction for retarding transmission of ultrasonic energy from said transducer to said conduit along said other directions, and
   acoustical lens means for focusing said transmitted energy to a focal zone and for shaping said reflected energy,
   said lens means including at least one inwardly-concave surface on the interior of said conduit in the path of said transmitted energy and
   said focal zone being spaced transversely from said concave surface a distance of not more than twice the transverse width of said conduit.

2. The device of claim 1 wherein said acoustic damping means comprises a plurality of closely-spaced small blind holes surrounding said transducer.

3. The device of claim 1 wherein said acoustical transducer is a piezoelectric crystal mounted in a blind hole in said conduit.

4. The device of claim 1 wherein said inwardly-concave surface is cylindrical and integral with a cylindrical interior surface of said conduit.

5. The device of claim 4 wherein said conduit is of methyl methacrylate and said focal zone is spaced from said lens surface by slightly less than the diameter of said conduit.

6. The device of claim 1 further comprising
   electrical pulse generating means for transmitting an electrical pulse to said acoustical transducer means to generate said transmitted ultrasonic energy during a first time period and
   electrical detecting means for detecting during a second time period following said first period electrical signals generated by said acoustical transducer means in response to said energy reflected from said particles.

* * * * *